US006979578B2

(12) United States Patent
Venugopal

(10) Patent No.: US 6,979,578 B2
(45) Date of Patent: Dec. 27, 2005

(54) PROCESS ENDPOINT DETECTION METHOD USING BROADBAND REFLECTOMETRY

(75) Inventor: Vijayakumar C. Venugopal, Berkeley, CA (US)

(73) Assignee: Lam Research Corporation, Fremont, CA (US)

( * ) Notice: Subject to any disclaimer, the term of this patent is extended or adjusted under 35 U.S.C. 154(b) by 6 days.

(21) Appl. No.: 10/401,118

(22) Filed: Mar. 27, 2003

(65) Prior Publication Data

US 2004/0032593 A1 Feb. 19, 2004

Related U.S. Application Data

(60) Provisional application No. 60/408,619, filed on Sep. 6, 2002, and provisional application No. 60/403,213, filed on Aug. 13, 2002.

(51) Int. Cl.⁷ .............................................. H01L 21/66
(52) U.S. Cl. ........................................................ 438/14
(58) Field of Search .......................... 359/369; 438/14; 356/400

(56) References Cited

U.S. PATENT DOCUMENTS

| | | | |
|---|---|---|---|
| 4,147,435 A | | 4/1979 | Habegger |
| 5,507,115 A | * | 4/1996 | Nelson ........................ 47/1.7 |
| 5,900,633 A | | 5/1999 | Solomon et al. |
| 5,936,734 A | | 8/1999 | Johs et al. |
| 5,980,768 A | | 11/1999 | Abraham |
| 6,111,634 A | | 8/2000 | Pecen et al. |
| 6,136,712 A | | 10/2000 | Klippert et al. |
| 6,160,621 A | | 12/2000 | Perry et al. |
| 6,271,047 B1 | | 8/2001 | Ushio et al. |
| 6,275,297 B1 | | 8/2001 | Zalicki |
| 6,373,573 B1 | * | 4/2002 | Jung et al. ................... 356/419 |
| 6,410,451 B2 | | 6/2002 | Nguyen et al. |
| 6,413,867 B1 | | 7/2002 | Sarfaty et al. |
| 6,567,213 B2 | * | 5/2003 | Rosencwaig et al. ....... 359/369 |
| 6,589,869 B2 | | 7/2003 | Sarfaty et al. |
| 6,608,681 B2 | * | 8/2003 | Tanaka et al. ............... 356/400 |
| 6,673,637 B2 | * | 1/2004 | Wack et al. .................. 438/14 |
| 6,856,384 B1 | * | 2/2005 | Rovira ......................... 356/73 |

FOREIGN PATENT DOCUMENTS

| | | |
|---|---|---|
| EP | 1111356 A2 | 6/2001 |
| JP | 2000292129 | 10/2000 |
| US | 02/90743 | 7/2002 |

OTHER PUBLICATIONS

PCT International Search Report, EPO, PCT/US03/25156.
Hicks et al., "Reflectance Modeling for In Situ Dry Etch Monitoring of Bulk $SiO_2$ and III–V multilayer structures" (Nov. 1994) Jrnl of Vac. Sc. & Tech. pp. 3306–3310.

(Continued)

Primary Examiner—John F. Niebling
Assistant Examiner—Andre' C. Stevenson
(74) Attorney, Agent, or Firm—IP Strategy Group, P.C.

(57) ABSTRACT

A method of determining a parameter of interest during processing of a patterned substrate includes obtaining a measured net reflectance spectrum resulting from illuminating at least a portion of the patterned substrate with a light beam having a broadband spectrum, calculating a modeled net reflectance spectrum as a weighted incoherent sum of reflectances from different regions constituting the portion of the patterned substrate, and determining a set of parameters that provides a close match between the measured net reflectance spectrum and the modeled net reflectance spectrum. For wavelengths below a selected transition wavelength, a first optical model is used to calculate the reflectance from each region as a weighted coherent sum of reflected fields from thin film stacks corresponding to laterally distinct areas constituting the region. For wavelengths above the transition wavelength, a second optical model based on effective medium approximation is used to calculate the reflectance from each region.

19 Claims, 15 Drawing Sheets

OTHER PUBLICATIONS

Bosch–Charpenay et al., "Real–Time Etch–Dept Measurements of MEMS Devices" (Apr. 2002) Jrnl of MicroElect. Sys., IEEE, NY, pp. 113–117.

Benson et al., "In–situ Spectroscopic Reflectometry for Polycrystalline Silicon Thin Film Etch Rate Determination during Reactive Ion Etching", (Jun. 1996) Jrnl of Elect. Mat., pp. 955–964.

Anon., "Zero–Order reflecting Reference Optics", (Jan. 1990) IBM Tech. Discl. Bulletin, pp. 381–383.

PCT International Search Report, PCT/US03/25146, dated Feb. 20, 2004.

P.A. Heimann and R.J. Schutz, "Optical etch–rate monitoring: computer simulation of reflectance," J. Electrochem. Soc. 131, pp. 881–885 (1984).

P.A. Heimann, "Optical etch–rate monitoring using active device areas: lateral interference effects," J. Electrochem. Soc. 132, pp. 2003–2006 (1985).

H.L. Maynard, N. Layadi, and J.T.–C. Lee, "Multiwavelength ellipsometry for real–time process control of the plasma etching of patterned samples," J. Vac. Sci. Technol. B 15, pp. 109–115 (1997).

W. Kong, H.–T. Huang, and F. L. Terry, Jr., "A hybrid analysis of ellipsometry data from patterned structures," Proceedings of NIST 2000, AIP Conference Proceedings, v. 550, pp. 373–377 (2001).

P. Lalanne and D.L. Lalanne, "On the effective medium theory of subwavelenght periodic structures," J. Mod. Opt. (1996).

V. C. Venugopal, A. Lakhtakia, R. Messier, and J.–P. Kucera, "Low permittivity nonocomposite materials using sculptured thin film technology," J. Vac. Sci. Technol. A 18, pp. 32–36 (2000).

G. Bouchitte and R. Petit, "Homogenization techniques as applied in the electromagnetic theory of gratings," Electromagnetics 5, pp. 17–36 (1985).

Z. R. Hatab, J.R. McNeil, and S. S. H. Naqvi, "Sixteen-megabit dynamic random access memory trench depth characterization using two–dimensional diffraction analysis," J. Vac. Sci. Technol. B 13, pp. 174–182 (1995).

* cited by examiner

"PROCESS ENDPOINT DETECTION METHOD USING BROADBAND REFLECTOMETRY"

CROSS REFERENCE TO RELATED APPLICATIONS

This application claims priority from and incorporates by reference the following provisional application(s) entitled "Endpoint Strategies for in situ Control of Recess and Deep Trench Etch Processes," filed "Aug. 13, 2002" (application Ser. No. 60/403,213) by inventor(s) Vijayakumar C. Venugopal and Andrew J. Perry and "Reflectrometry-based Approaches For in situ Monitoring of Etch Depths in Plasma Etching Processes, " filed Sep. 6, 2002 (application Ser. No. 60/408,619) by inventor(s) Vijay C. Venugopal and Andrew J. Perry. This application also claims priority from and incorporates by reference the following non-provisional application(s) entitled "Method for In-Situ Monitoring of Patterned Substrate Processing Using Reflectrometry," filed Nov. 1, 2002 (application Ser. No. 10/286,410) by inventor(s) Vijayakumar C. Venugopal and Andrew J. Perry and "Method for Controlling A Recess Etch Prcoess," filed Nov. 1, 2002 (application Ser. No. 10/286,409) by inventor(s) Andrew J. Perry and Vijayakumar C. Venugopal.

BACKGROUND OF THE INVENTION

The invention relates generally to methods for monitoring and controlling processes used in forming features on semiconductor substrates. More specifically, the invention relates to a method for detecting an endpoint in semiconductor substrate processing.

In semiconductor manufacturing, various combinations of processes such as etching thin-film deposition, and chemical-mechanical polishing are used to form features on a semiconductor substrate. The features are formed by selectively removing materials from and selectively depositing materials on the surface of the semiconductor substrate. While forming the features, the semiconductor substrate is monitored to determine when an endpoint has been reached in the process. An endpoint could be a point at which the process conditions should be changed or a point at which the process should be stopped.

Deep trench and recess etch processes are used in fabrication of semiconductor devices such as dynamic random access memory (DRAM) and embedded DRAM (eDRAM). A DRAM (or eDRAM) cell contains transistors and capacitors for storing information. Typically, the storage capacitors are installed in trenches in a semiconductor substrate. A typical process for forming a trench capacitor involves etching a deep trench in a semiconductor substrate, filling the trench with polysilicon, and etching down the polysilicon to form a recess in the trench. Other materials, such as a dielectric material, may also be deposited in the trench or recess and etched as necessary to form a desired storage structure. Typically, the trench has a high aspect ratio (i.e., greater than 1.0, where "aspect ratio" is defined as height/width). In the current technology, for example, the depth of the trench is, typically several microns deep, while the width of the trench is typically on the order of 300 nm. As advances are made in integration technology, the width of the trench is expected to get even smaller, e.g., shrink down to 90 to 100 nm.

FIG. 1A shows a typical semiconductor substrate 100 having a substrate layer 102, typically made of silicon, a pad layer 104, typically made of silicon dioxide, and a mask layer 106, typically made of silicon nitride. A thin film of photoresist mask 108 may also be deposited on the mask layer 106. Prior to forming a deep trench in the substrate 100, an area 110 of the photoresist mask 108 where the trench will be formed is removed, causing the underlying layer, i.e., the mask layer 106, to become exposed. The substrate 100 is then placed in a process chamber (not shown), such as a plasma chamber, and the trench is etched through the mask layer 106 and pad layer 104 into the substrate layer 102. FIG. 11B shows a trench 112 etched in the substrate 100. After etching the trench 112 in the substrate 100, the remaining photoresist mask (108 in FIG. 1A) is removed.

FIG. 1C shows the trench 112 in the substrate 100 backfilled with polysilicon 114. During the backfill process, a blanket of polysilicon 116 is formed over the mask layer 106. Typically, a small dish (or depression) 118 appears above the opening of the trench 112 as a consequence of the backfill process. Before forming a recess in the polysilicon 114 in the trench 112, all or a portion of the blanket of polysilicon 116 is removed by a planarization process, such as planar layer etching or chemical-mechanical polishing. FIG. 1D shows the substrate 100 after the planarization process. A depression 120 may appear above the opening of the trench 112 as a consequence of the planarization process. After the planarization steps the polysilicon column 114 in the trench 112 is etched down to a predetermined depth to form a recess. FIG. 1E shows a recess 122 formed above the polysilicon column 114.

The depth of the recess 122 relative to a reference point in the substrate 100, e.g., the bottom of the sacrificial mask layer 106, is usually a critical dimension. However, various factors make it challenging to accurately form a recess having a desired depth. One factor is that the opening of the trench through which the recess is etched is very tiny, e.g., on the order of 300 nm or less. Thus, the etch process must be carefully controlled to ensure that the etching is confined to the trench. Another factor is that the depression above the polysilicon column can easily be on the same order as the accuracy or even the absolute depth of the recess to be etched. Thus, the dimensional control limits are very tight. Another factor is that there are incoming material variations from one substrate to another, e.g., variations in thickness of the mask layer (e.g., as a result of the planarization process) and the depth of the depression above the polysilicon column. Without knowledge of these variations, it would be difficult to determine how far down to etch the polysilicon to make the required recess depth.

In order to accurately form a recess of a desired depth, it is important to have an accurate and reliable method of detecting an endpoint in the etching process. Optical diagnostic methods are typically used to detect endpoints in patterned substrate processing because they are non-intrusive. Optical emission spectroscopy is the most widely used optical diagnostic method for detecting an endpoint. The method involves monitoring plasma emissions for a change in the species of the plasma, where a change occurs when moving from one layer of the substrate to another layer. The response of this method is typically delayed because it monitors the plasma state instead of the substrate state. Optical emission spectroscopy is generally unsuitable for deep trench and recess etching as well as other etch applications where there is no effective etch stop layer.

Single-wavelength interferometry is another example of an optical diagnostic method that is used to detect an endpoint. The interferometry approach involves directing a light beam on the substrate surface. The reflected signals from the substrate combine constructively or destructively to produce a periodic interference fringe as a film, trench or, recess is being etched. The phase of the interference fringe depends on the path length of the light beam through, the thickness of the layer being etched. During etching, the observed number of periods of a measured interference fringe is correlated with; a calculated reduction in the thickness of the layer or the change in the depth of the trench or recess being etched to estimate an endpoint in the process. The interferometric endpoint detection method involves counting the number of fringes evolved during the etch. When a predetermined number of fringes corresponding to the thickness of material to be removed has been counted, the etching process is stopped.

Single-wavelength interferometric approaches are limited in their ability to monitor etching applications such as recess etching. One reason for this is that they monitor relative changes in vertical dimensions of structures on the substrate as opposed to absolute vertical dimensions of structures. Thus, they cannot compensate for incoming material variations from one substrate to another, such as variation in thickness of mask layer, variation in starting depth of trenches, variation in pattern densities, and variation in wafer orientation. As previously mentioned, without knowing these incoming material variations, it would be difficult to accurately determine how much material to remove via etching. Another reason is that as the structures get smaller (e.g., smaller than the wavelength of the incident light) and deeper the contrast of the fringes evolved from the substrate drops and any small noise can wash out the fringes, making it impossible to determine when an endpoint has been reached in the process.

Spectroscopic ellipsometry, polarimetry, and reflectometry are examples of optical diagnostic methods that can be used in conjunction with rigorous optical modeling techniques to determine the absolute vertical and lateral dimensions of features of special test structures such as one-dimensional gratings on a patterned substrate. However, these techniques are limited to inline meteorology applications (i.e., pre-and post-processing meteorology) rather than in situ diagnostics since they involve measurements only on special test structures and also a significant computational load. Efforts have been made to combine the use of spectroscopic ellipsometry and simple, considerably less accurate, modeling techniques for in situ diagnostics.

From the foregoing, there is desired a robust, easy-to-use, and accurate method for in situ diagnostics that will facilitate detecting an endpoint in substrate processing even when the structures of interest are, much smaller than the wavelength of the incident light.

SUMMARY OF THE INVENTION

In one aspect, the invention relates, to a method of determining a parameter of interest during processing of a patterned substrate which comprises obtaining a measured net reflectance spectrum resulting from illuminating at least a portion of the patterned substrate with a light beam having a broadband spectrum and calculating a modeled net reflectance spectrum as a weighted incoherent sum of reflectances from different regions constituting the portion of the patterned substrate. For wavelengths below a selected transition wavelength in the broadband spectrum, a first optical model is used to calculate the reflectance from each region as a weighted coherent sum of reflected fields from thin film stacks corresponding to laterally distinct areas constituting the region. For wavelengths above the selected transition wavelength in the broadband spectrum, a second optical model is used to calculate the reflectance from each region as a reflected field from a thin film stack obtained by replacing layers in the region with effective homogeneous mediums. The method further includes determining a set of parameters that provides a close match between the measured net reflectance spectrum and the modeled net reflectance spectrum.

In another aspect, the invention relates to a method for controlling processing of a patterned substrate which comprises obtaining a measured net reflectance spectrum resulting from illuminating at least a portion of the patterned substrate with a light beam having a broadband spectrum and calculating a modeled net reflectance spectrum as a weighted incoherent sum of reflectances from different regions constituting the portion of the patterned substrate. For wavelengths below a selected transition wavelength in the broadband spectrum, a first optical model is used to calculate the reflectance from each region as a weighted coherent sum of reflected fields from thin film stacks corresponding to laterally distinct areas constituting the region. For wavelengths above the selected transition wavelength in the broadband spectrum, a second optical model is used to calculate the reflectance from each region as a reflected field from a thin film stack obtained by replacing layers in the region with effective homogeneus mediums. The method further includes determining a set of parameters that provides a close match between the measured net reflectance spectrum and the modeled net refletance spectrum, deriving a parameter of interest from the set of parameters, and signaling an endpoint in the processing of the patterned substrate if the value of the parameter of interest satifies a predetermined endpoint criterion.

These and other features and advantages of the invention will be discussed in more detail in the following detailed description of the invention and in conjunction with the following figures.

BRIEF DESCRIPTION OF THE DRAWINGS

The invention is illustrated by way of example, and not by way of limitation, in the figures accompanying the drawings, and in which like reference numerals refer to similar elements, and in which.

DETAILED DESCRIPTION OF THE PREFERRED EMBODIMENTS

Figure 1A:
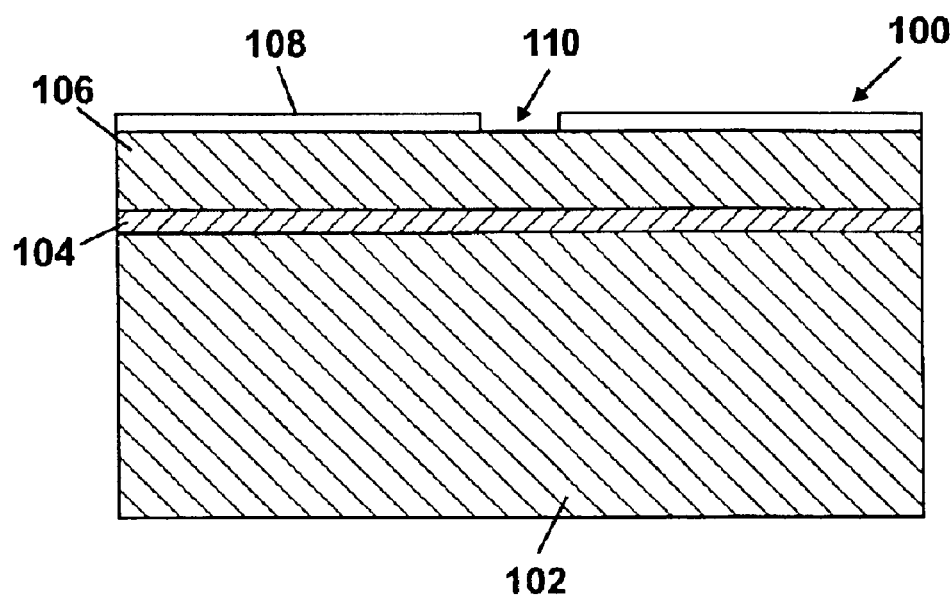
FIG. 1A is a transverse cross-section of a semiconductor substrate.
Figure 1B:
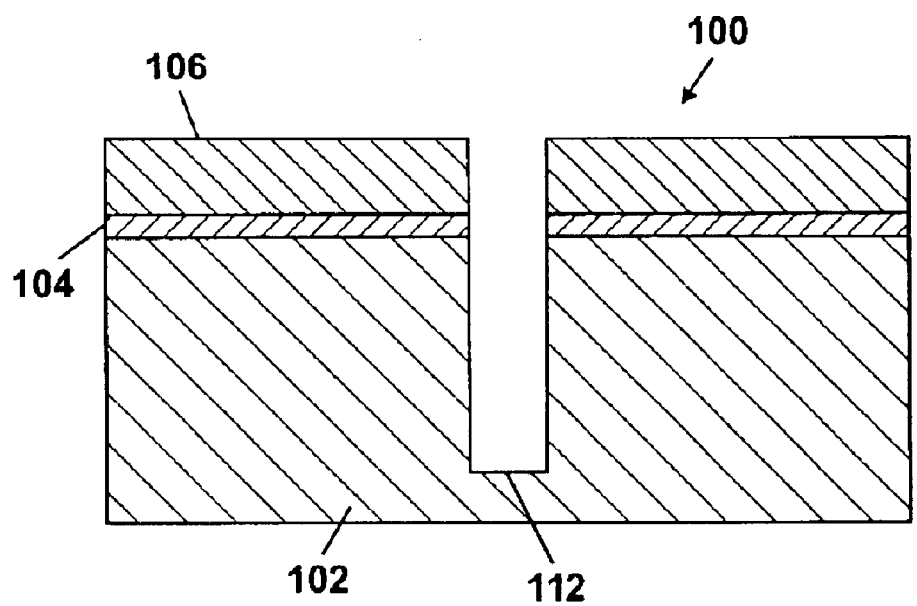
FIG. 1B shows a trench etched in the semiconductor substrate of FIG. 1A.
Figure 1C:
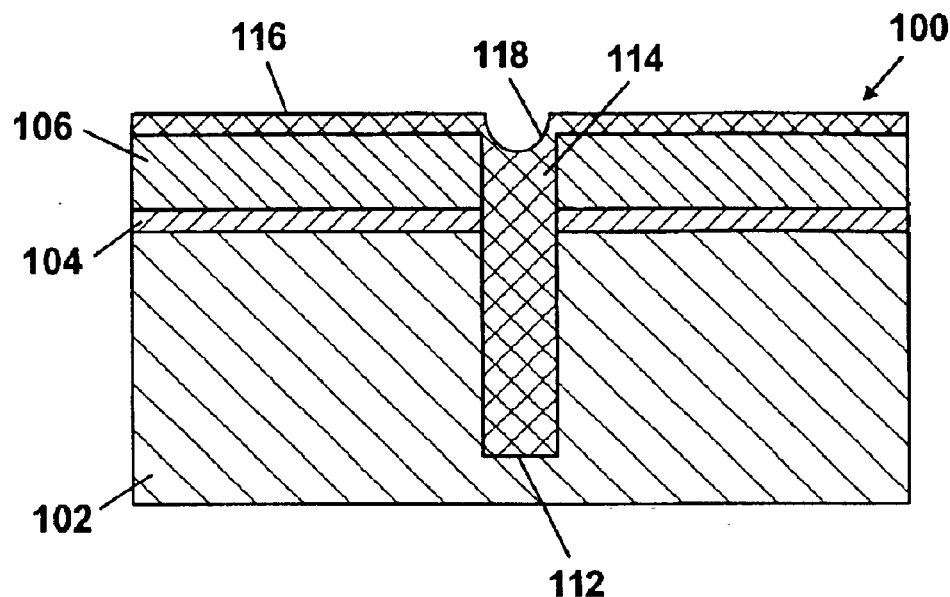
FIG. 1C shows the trench of FIG. 1B backfilled with polysilicon.
Figure 1D:
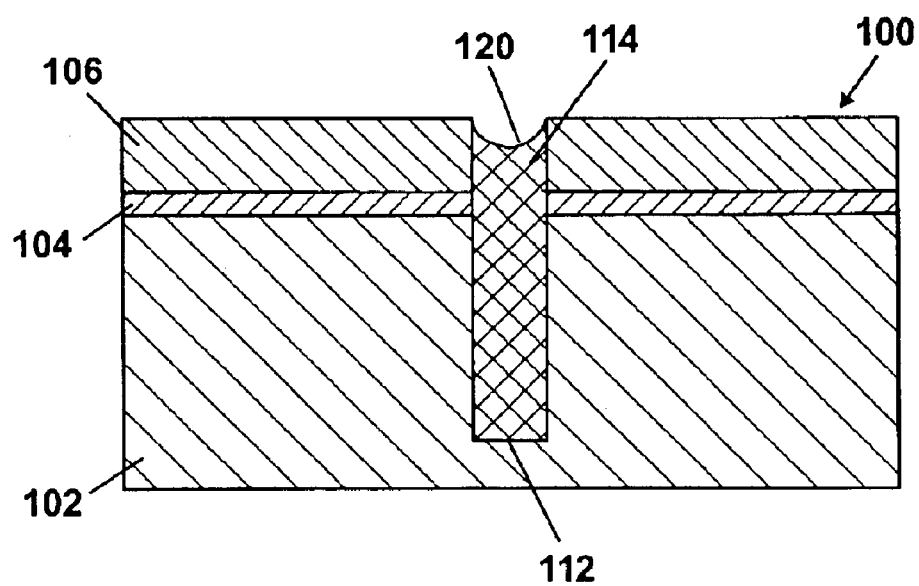
FIG. 1D shows the semiconductor substrate of FIG. 1C after planarization.
Figure 1E:
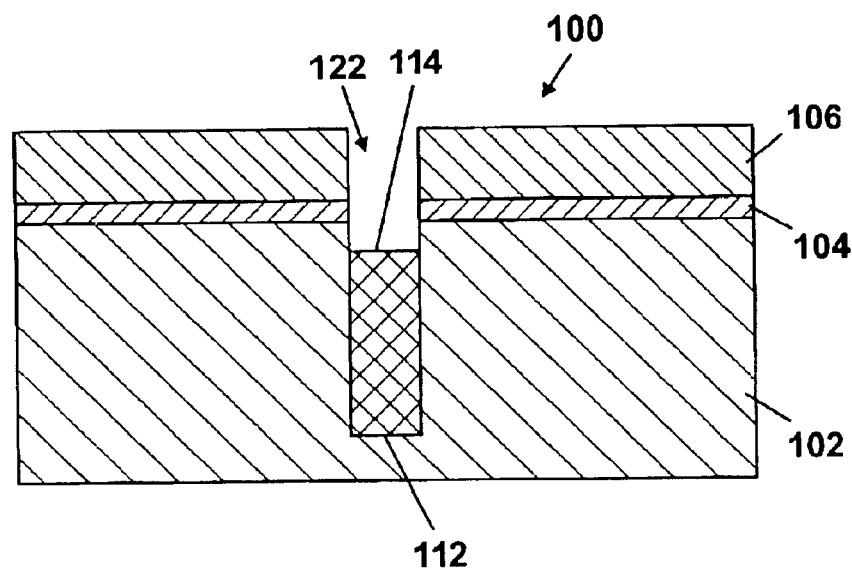
FIG. 1E shows a recess formed in the trench of FIG. 1D.

The invention will now be described in detail with reference to a few preferred embodiments, as illustrated in the accompanying drawings. In the following description, numerous specific details are set forth in order to provide a thorough understanding of the invention. It will be apparent, however, to one skilled in the art, that the invention may be practiced without some or all of these specific details. In other instances, well-known process steps and/or features have not been described in detail in order to not unnecessarily obscure the invention. The features and advantages of the invention may be better understood with reference to the drawings and discussions that follow.

In one embodiment of the invention, broadband reflectometry is used to measure the reflectance from a patterned substrate while the patterned substrate is being processed. The reflectometry approach involves illuminating the patterned substrate with broadband light and collecting reflectance data from the patterned substrate. The collected reflectance data is used to generate a measured net reflectance spectrum of the patterned substrate. A set of parameterized quantities of interest is then obtained by matching the measured net reflectance spectrum to a net reflectance spectrum obtained from optical reflectance modeling of the patterned substrate. An endpoint criterion is applied to one or more of the parameterized quantities to determine if an endpoint has been reached in the patterned substrate processing. If an endpoint has been reached, an endpoint signal is generated, where an endpoint signal could indicate that the process conditions be changed or that the processing of the patterned substrate be stopped.

While not wishing to be bound by theory, the inventor believes herein that when using incident light having a broadband spectrum, i.e., a large range of wavelengths, to make reflectometry measurements, there will be a transition wavelength in the broadband spectrum below which the incident light can resolve features on patterned substrate and above which the incident light has reduced capability to resolve individual features on the patterned substrate. The inventor believes that the transition wavelength is; functionally dependent on the lateral dimensions and vertical dimensions of the dominant features on the patterned substrate. At wavelengths below the transition wavelength, the free-space wavelength of the incident light is comparable to or smaller than the characteristic size of the dominant features on the patterned substrate. For illustration purposes, "comparable" may be considered to be up to 2.0 times the characteristic size of the dominant features on the patterned substrate. The characteristic size of dominant features on the patterned substrate may be for instance, the size of the recess or trench openings. What is deemed to be comparable may generally be determined empirically or in-situ. At wavelengths above the transition wavelength, the free-space wavelength of the incident light is much larger than the characteristic size of the dominant features on the patterned surface. For illustration purposes, "much larger" may be considered to be greater than 2.0 times the characteristic size. Again, What is deemed to be "much larger" may generally be determined empirically or in-situ.

Therefore, in order to optimally match the measured net reflectance spectrum to the modeled net reflectance spectrum the inventor believes herein that two optical reflectance models are needed, one, for calculating net reflectance at wavelengths below the transition. wavelength and another for calculating net reflectance at wavelengths above the transition wavelength. The optical reflectance model valid at wavelengths below the transition wavelength is referred to herein as the "partial coherence reflectance" model. The optical reflectance model valid at wavelengths above the transition wavelength is referred to herein as the "effective medium approximation" model.

Both the partial coherence reflectance model and the effective medium approximation model involve calculating the net reflectance spectrum from the patterned substrate as a weighted incoherent sum of reflectances from different regions constituting the pattern. In the case of the partial coherence reflectance, model, the reflectance from each region may be a weighted coherent sum of reflected fields from laterally distinct areas constituting the region, where each laterally distinct area is an isotropic, homogeneous, thin film stack. In the case of the effective medium approximation model, vertically-distinct layers in each region are replaced with optically-equivalent homogeneous mediums using homogenization formalisms. The reflectance of the region is then set to the reflected field from the stack of homogeneous mediums.

A common goal in both the partial coherence reflectance model and the effective medium approximation model is to model the patterned substrate as a collection of thin film stacks. This is because the reflected field for a thin film stack illuminated by a plane wave of known intensity and polarization can be readily calculated by setting up and solving a boundary value problem using Maxwell's equations or, equivalently, by applying Fresnel equations.

Figure 2:
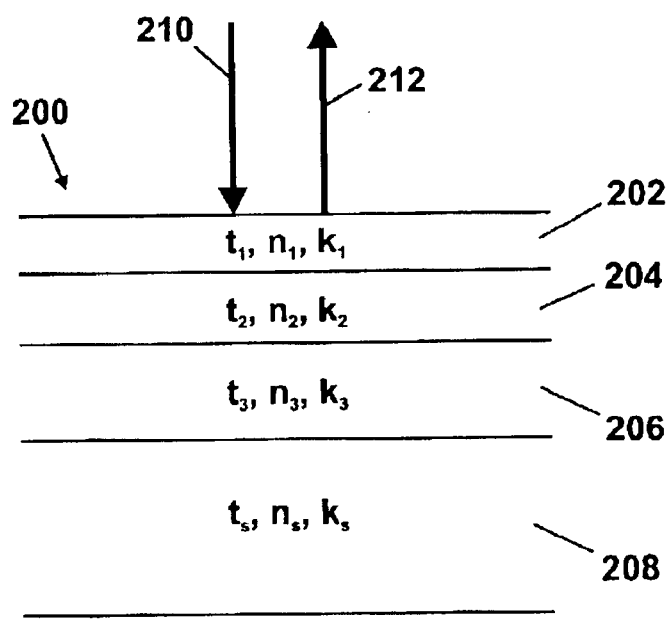
FIG. 2 is a generalized schematic of a thin film stack.

For illustration purposes, FIG. 2 shows a thin film stack 200 having layers 202, 204, 206, and 208. As an example, the layer 202 could be a photoresist mask layer, the layer 204 could be a hard mask layer, the layer 206 could be a pad oxide layer, and the layer 208 could be a substrate layer. Each of the layers 202, 204, 206, 208 has a thickness (t), a refractive index (n), and an extinction coefficient (k). Reflectance measurements are made by illuminating the thin film stack 200 at normal incidence with a light beam 210 and collecting the light beam 212 reflected normally from the thin film stack 200. The thin film stack 200 is assumed to have an infinite lateral extent, and the reflected light beam 212 depends on the optical properties of all the layers that form the thin film stack 200.

For the partial coherence reflectance model, the patterned substrate is divided into m≧1 laterally distinct areas, and each laterally distinct area is modeled as an isotropic; homogeneous, thin film stack. For normal incidence reflectometry, the response of an isotropic, homogeneous, thin film stack is nominally polarization independent. Given the random array of feature sizes and orientations that constitute a typical pattern on a semiconductor substrate, the, inventor believes herein that the patterned substrate can also be assumed to have a nominally polarization-independent reflectance, which greatly simplifies the computational aspects of the model. It must be noted, however, that the technique can be easily adapted to model a polarization-dependent response too. For example, this may indeed be the case when the distribution of features constituting the pattern is known to be predominantly oriented in one direction within the plane of the patterned substrate.

Figure 3A:
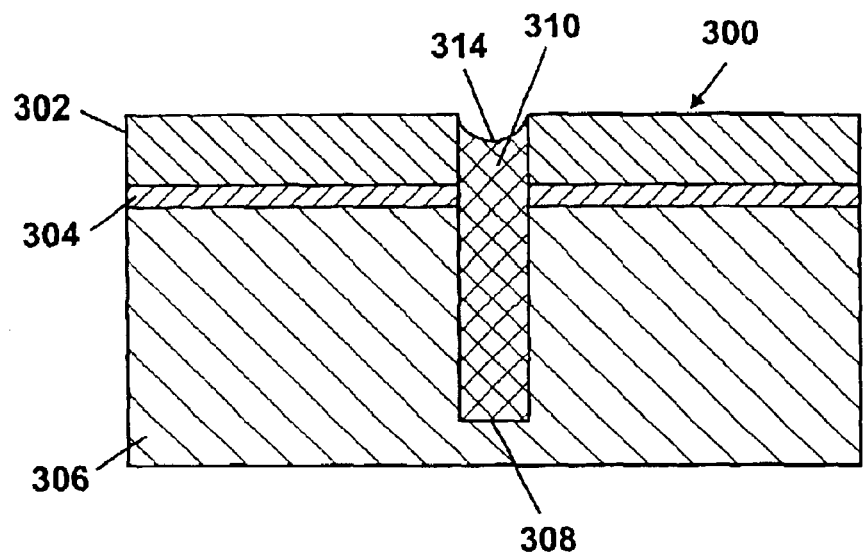
FIG. 3A is a transverse cross-section of a patterned substrate used in illustrating an embodiment of the partial coherence reflectance model of the invention.
Figure 3B:
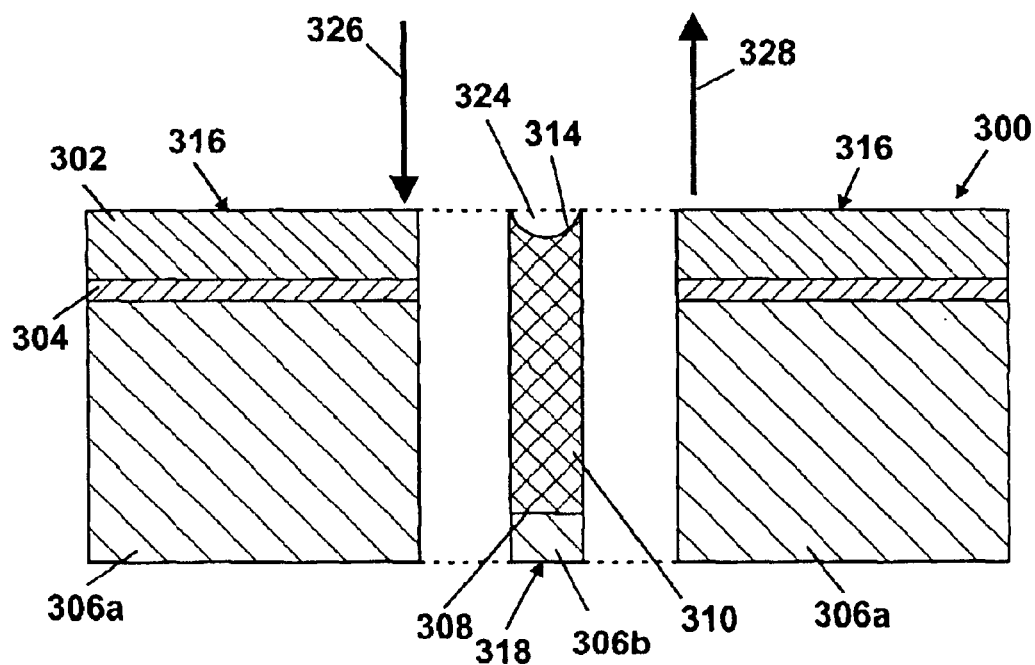
FIG. 3B shows the patterned substrate of FIG. 3A divided into two laterally distinct areas.

For the partial coherence reflectance model, the main factors defining lateral distinctness are differences in composition and thicknesses of layers constituting the thin film stacks. For example, FIG. 3A shows a transverse cross-section of a patterned substrate 300 having a mask layer 302, an oxide layer 304, and a substrate layer 306. A trench 308 is formed in the substrate 300 and filled with polysilicon 310. A small depression 314 is formed at the top of the polysilicon column 310 in the trench 308 as a consequence of the filling process and/or planarization process. FIG. 3B shows the patterned substrate 300 divided into two laterally distinct areas 316, 318. Each laterally distinct area is also an isotropic, homogeneous, thin film stack. The thin film stack 316 includes the mask layer 302, the oxide layer 304, and a substrate layer portion 306a. The thin film stack 318 includes the polysilicon column 310 and a substrate layer portion 306b.

Figure 3C:
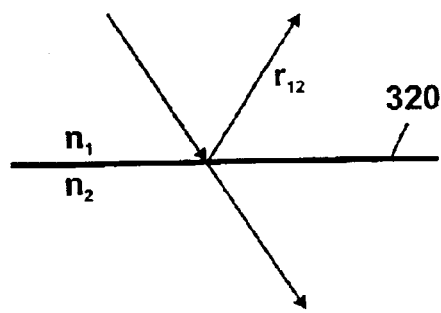
FIG. 3C shows a reflectance model for a layer interface.

The reflectance of the patterned substrate 300 is a combination of the reflected fields from the thin film stacks 316, 318. The reflected field for a given thin film stack illuminated by a plane wave of known intensity and polarization can be calculated by setting up and solving a boundary problem using Maxwell's equations or by using Fresnel equations. For example, using Fresnel equations, the reflectance at a layer interface (320 in FIG. 3C) is given by:

$$r_{12} = \frac{n_1 - n_2}{n_1 + n_2} \tag{1}$$

Figure 3D:
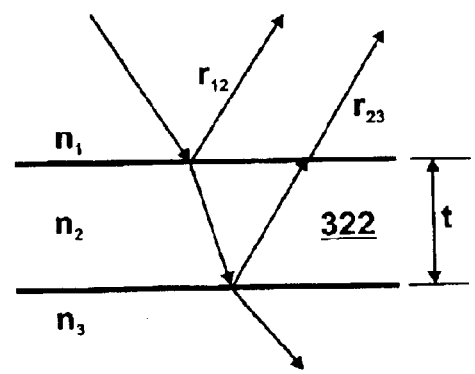
FIG. 3D shows a reflectance model for a single layer.

The reflected field for a single layer (322 in FIG. 3D) is given by:

$$r_{123} = \frac{r_{12} - r_{23} e^{i4\lambda_0 n_2 t}}{1 + r_{12} r_{23} e^{i4\lambda_0 n_2 t}} \tag{2}$$

Returning to FIG. 3B, for the purposes of calculating net reflectance of the patterned substrate 300, the heights of the thin film stacks 316, 318 should be the same. A layer of air or vacuum 324 is added to the top of the column of polysilicon 310 to compensate for the difference in the heights of the thin film stacks 316, 318.

For the partial coherence reflectance model, the inventor believes herein that given the distribution of the lateral extents of features constituting a typical patterned substrate, the reflected fields from the patterned substrate are likely to add coherently over some regions of the pattern and incoherently over some other regions of the pattern. The inventor believes herein that the relative contributions of the coherently and incoherently combined fields could vary as a function of free-space wavelength, $\lambda_0$, and do not necessarily correspond to the actual area fractions on the patterned substrate. Thus, the net reflectance from a patterned substrate can be calculated as a weighted incoherent sum of reflectances from n different regions constituting the pattern:

$$R = w_1(\lambda_0)|E_1|^2 + w_2(\lambda_0)|E_2|^2 + \ldots + w_n(\lambda_0)|E_n|^2 \tag{3}$$

where R is the net reflectance measured, $E_i$ are the individual incoherently adding field terms, and $w_i(\lambda_0)$ are the weighting factors for the incoherently adding terms. The use of $|E_i|^2$ denotes the magnitude of the complex field $E_i$ in the frequency domain notation of electromagnetic field theory.

Each individual incoherently adding term in equation (3) could be the weighted, coherent sum of fields from k laterally distinct areas constituting the $i^{th}$ region on the substrate:

$$E_i = \alpha_1(\lambda_0)E_{c1} + \alpha_2(\lambda_0)E_{c2} + \ldots + \alpha_k(\lambda_0)E_{ck} \tag{4}$$

where $\alpha_i(\lambda_0)$ are the weighting factors for coherently adding field terms $E_{ci}$. It should be noted that in equations (3) and (4), a "region" is not the same as a "laterally distinct area."

Figure 3E:
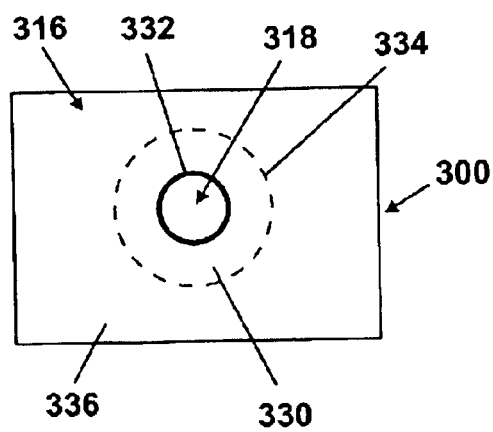
FIG. 3E is a top view of the patterned substrate shown in FIG. 3A.

To further illustrate how the partial coherence reflectance model works, consider the patterned substrate 300 shown in FIG. 3B. The patterned substrate 300 has been divided into two laterally distinct areas or thin film stacks 316, 318. In operation, an incident light beam 326 strikes the patterned substrate 300 and is reflected, as shown at 328. The lateral extent of the trench 308, which is a dominant feature on the patterned substrate 300, is comparable to or larger than the wavelength of the incident light beam 326. FIG. 3E shows a top view of the patterned substrate 300. Let $r_1$ represent the reflected field due to, the thin film stack 316 and $r_2$ represent the reflected field due to the thin film stack 318. The inventor proposes herein that there is a region 330 overlapping the boundary 332 between the thin film stacks 316, 318, demarcated by, imaginary line 334, where the reflection fields $r_1$ and $r_2$ would add coherently because of lateral interference effects. The reflectance from the region 336 outside of the imaginary line 334 is expected to be due to the reflected field from the thin film stack 316 only.

From equation (3), the net reflectance from the patterned substrate 300 is:

$$R_{300} = w_{336}(\lambda_0)|E_{336}|^2 + w_{330}(\lambda_0)|E_{330}|^2 \tag{5}$$

where $R_{300}$ is the net reflectance from the patterned substrate 300, $E_{330}$, $E_{336}$ are the individual incoherently adding field terms from the regions 330, 336, respectively, and $w_{330}(\lambda_0)$, $w_{336}(\lambda_0)$, are the weighting factors for the incoherently adding terms. From equation (4), $E_{330}$ is:

$$E_{330} = \alpha(\lambda_0)E_{336} + (1-\alpha(\lambda_0))E_{318} \tag{6}$$

It should be noted that $E_{336}$ is $r_1$, $E_{318}$ is $r_2$, and $w_{330}$ can be rewritten as $(1-w_{336})$. Thus, equation (5) can be rewritten as:

$$R_{300} = w_{336}(\lambda_0)|r_1|^2 + (1-w_{336}(\lambda))|\alpha(\lambda_0)r_1 + (1-\alpha(\lambda_0))r_2|^2 \tag{7}$$

Equations (3) and (4) provide a simplified model wherein reflectance from a patterned substrate can be parameterized with respect to several quantities of interest, such as mask layer thickness and starting etch depth. In one embodiment, the invention uses normal incidence reflectometry as a technique for measuring reflectance, meaning the patterned substrate is illuminated by a beam incident normal to the substrate and only the light reflected normal to the substrate is collected, i.e., only specularly reflected light is collected. However, because a range of orientations can be seen in any pattern, not all of the light stinking the pattern will reflect at normal incidence. There will be non-specular reflection due to, for example, the depression (314 in FIG. 3A). Reflection losses due to such non-specular reflection should not be ignored. In an embodiment of the invention, a scattering loss factor is applied to parts of the adding terms in equation (3) or to the entire reflectance in equation (3). The scattering loss factor could be a function of free-space wavelength, $\lambda_0$.

For the effective medium approximation model, the patterned substrate is divided into paternally distinct regions. A "laterally distinct region" in the context of the partial coherence reflectance model is an isotropic, homogeneous thin film stack. In the effective medium approximation model, a laterally distinct region is defined as: (1) a relatively large extent region of a blanket film stack, or (2) a region reasonably densely populated by the presence of features having lateral dimensions much smaller than the free-space wavelength of the incident light or by the presence of features having high aspect ratios, e.g., greater than 1.0, or both, such as common to trench capacitors. Generally speaking, to model the latter set of regions as homogeneous thin film stacks, the regions are first divided into vertically-distinct layers. Then, the vertically-distinct layers are replaced with effective homogeneous mediums, where the structures can be modeled as inclusions in a host medium.

Figure 4A:
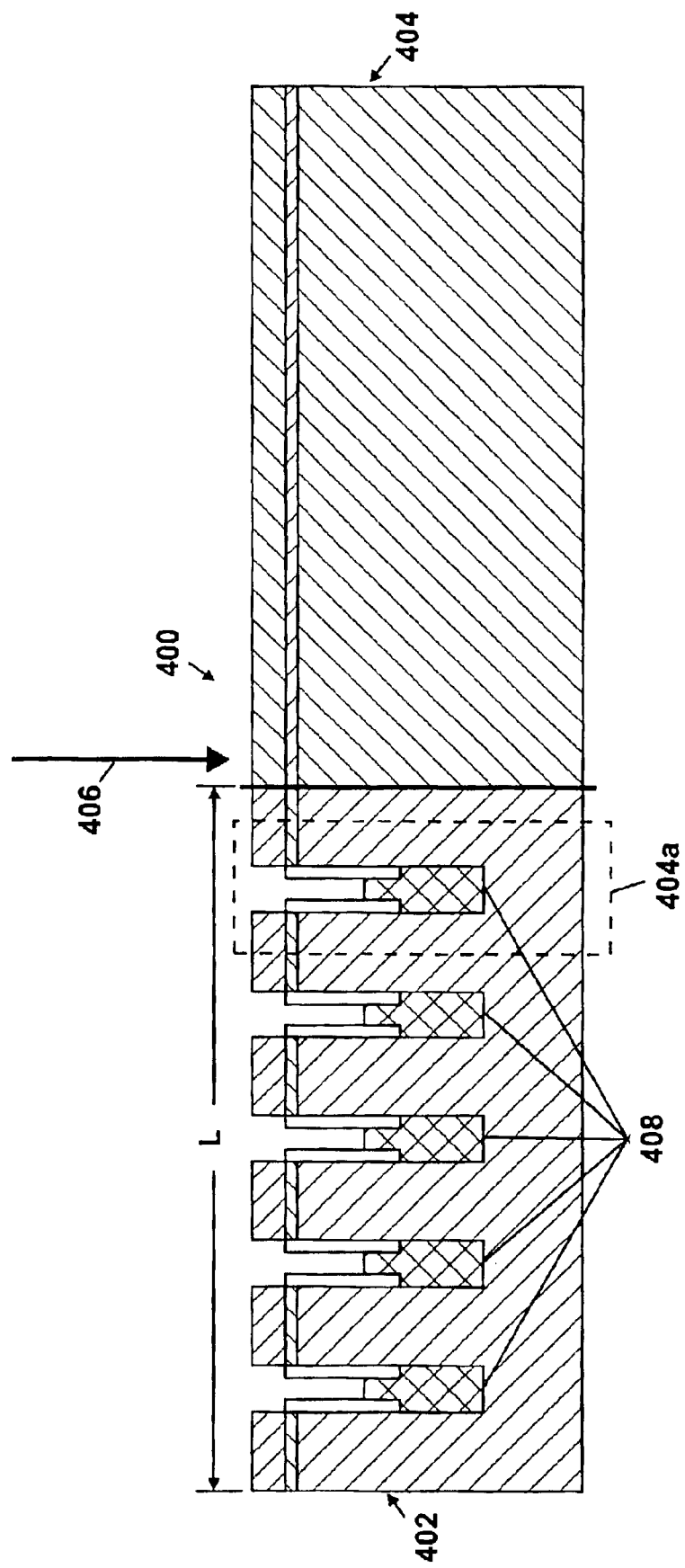
FIG. 4A is a transverse cross-section of a substrate divided into two laterally distinct regions.

For illustration purposes, FIG. 4A shows a patterned substrate 400 divided into two laterally distinct regions 402, 404. Each of the regions 402, 404 has a lateral extent (L) that is much greater than the free-space wavelength of the incident light 406. The region 402 is densely populated with trenches 408 while the region 404 consists of a blanket thin, film stack. The trenches 408 are assumed to have lateral extents (or dimensions) much smaller than the free-space wavelength of the incident light 406. There are no hard limits on how much smaller the lateral extent of the trenches 408 can be relative to the free-space wavelength of the incident light 406. For example, the lateral extent of the trenches could be 10 to 100 times smaller than the free-space wavelength of the incident light 406. The trenches 408 could also have high aspect ratios.

Using effective medium approximation, a laterally distinct region can be effectively modeled as a thin film stack having multiple layers of homogeneous mediums without openings. High-aspect ratio structures, if present, can be modeled as needle-shaped inclusions, or cylindrical inclusions, in the host medium. The response property of the thin film stack is dependent on the shape of the inclusions in the host medium. In general, the response property could be uniaxial or biaxial anisotropic. For example, if the inclusions have a circular cross-section, the response property is uniaxial anisotropic, and if the inclusions have an elliptical cross-section, the response property is biaxial anisotropic. What is meant by unlaxial response is that each layer of the thin film stack has a certain refractive index in the thickness direction of the film that is different from the effective refractive index within the plane of the film. Thus, optically speaking, the thin film stack behaves differently in different directions within the thickness of the film. In the case of the biaxial response, there could be differences within the thickness and the plane of the film. The consequence of the biaxial anisotropic response is that there is a polarization dependence which must be factored into calculation of the reflectance from the thin film stack. In the case of uniaxial response, the response to excitation by normally incident light can be assumed to be nominally polarization independent.

Figure 4B:
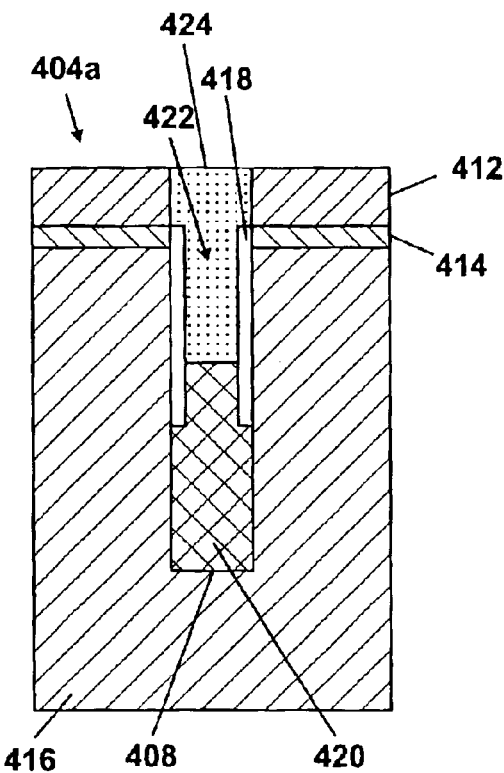
FIG. 4B is an enlarged section of the patterned area of the substrate shown in FIG. 4A.

A process of modeling the laterally distinct region 402 as a homogeneous thin film stack will now be described. For illustrative purposes, FIG. 4B shows an enlargement of a section (404a in FIG. 4A) of the laterally distinct region 402. As shown in FIG. 4B, the section 404a includes a mask layer 412, an oxide layer 414, and a substrate layer 416. A trench 408 is etched through the mask layer 412 and oxide layer 414 into the substrate layer 416. A dielectric collar 418 and a polysilicon column 420 are installed in the trench 408, and a recess 422 is formed in the trench 408, above the polysilicon column 420. For the purpose of optical modeling, a column of air (or vacuum) 424 is assumed to be present above the polysilicon column 420.

Figure 4C:
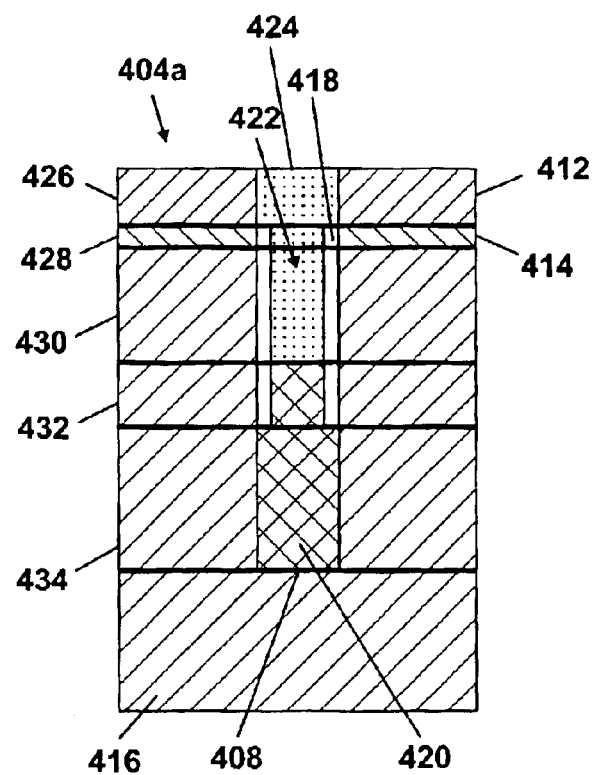
FIG. 4C shows the enlarged section of FIG. 4A divided into vertically-distinct layers.

The section 404a can be divided into q vertically-distinct layers. For example, FIG. 4C shows the section 404a divided into vertically-distinct layers 426, 428, 430, 432, and 434. Each layer is a composite layer. The layer 426 includes the mask layer 412. and a portion of the air column 424 and has a thickness ($t_1$) equal to the thickness of the mask layer 412. The layer 428 includes the oxide layer 414 and a portion of the air column 424 and has a thickness ($t_2$) equal to the thickness of the oxide layer 414. The layer 430 includes a portion of the dielectric collar 418, a portion of the substrate layer 416, and a portion of the air column 424 and has a thickness ($t_3$) equal to a vertical distance from the bottom of the oxide layer 414 to the top of the polysilicon column 420. The layer 432 includes a portion of the dielectric collar 418, a portion of the polysilicon column 420, and a portion of the substrate layer 416 and has a thickness ($t_4$) equal to a vertical distance from the top of the polysilicon column 420 to the bottom of the dielectric collar 418. The layer 434 includes a portion of the substrate layer 416 and a portion of the polysilicon column 420 and has a thickness ($t_5$) equal to a vertical distance from the bottom of the dielectric collar 418 to the bottom of the trench 408.

Figure 4D:
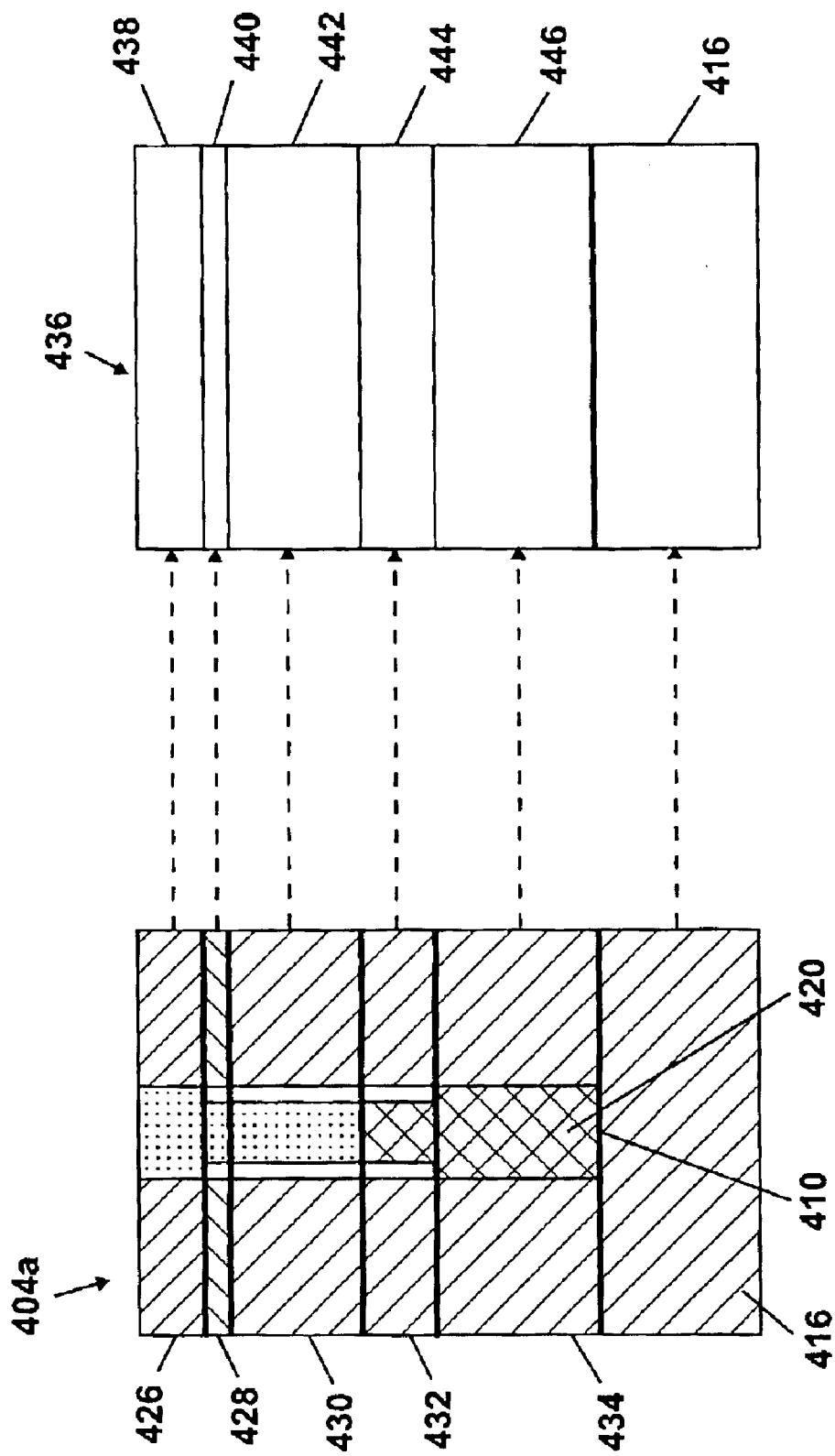
FIG. 4D shows a thin film stack formed by homogenizing vertically-distinct layers in an area on a patterned substrate.

FIG. 4D shows a thin film stack 436 including homogeneous layers 438, 440, 442, 444, and 446 corresponding to the composite layers 426, 428, 430, 432, and 434, respectively, in the section 404a. The effective optical properties of a homogeneous layer are determined based on the optical properties and the volume fractions of the component mediums in the corresponding composite layer.

The component mediums in the layer 426 are the mask material and air. The effective refractive index of the homogeneous layer 438, corresponding to the composite layer 426, can be expressed as:

$$\tilde{n}_1 = f_1(\tilde{n}_{mask}, n_{air}, V_{mask}) \quad (8)$$

where the $\tilde{n}_1$ represents the complex refractive index of the homogeneous layer 438, $\tilde{n}_{mask}$ represents the complex refractive index of the mask medium, $n_{air}$ represents the refractive index of air and has a value of 1, and $V_{mask}$ represents the volumetric proportion of the mask medium.

The component mediums in the layer 428 are oxide and air. The effective refractive index of the homogeneous layer 440, corresponding to the composite layer 428, can be expressed as follows:

$$\tilde{n}_2 = f_2(\tilde{n}_{oxide}, n_{air}, V_{oxide}) \quad (9)$$

where $\tilde{n}_2$ represents the complex refractive index of the homogeneous layer 440, $\tilde{n}_{oxide}$ represents the complex refractive index of the oxide medium, n$_{air}$ represents the refractive index of air and has a value of 1, and V$_{oxide}$ represents the volumetric proportion of the oxide medium.

The component mediums in the layer 430 are the substrate material, the dielectric material, and air. The effective refractive index of the homogeneous layer 442, corresponding to the composite layer 430, can be expressed as follows:

$$\tilde{n}_3 = f_3(\tilde{n}_{substrate}, \tilde{n}_{dielectric}, n_{air}, V_{substrate3}, V_{dialectric3}) \quad (10)$$

where $\tilde{n}_3$ represents the complex refractive index of the homogeneous layer 442, $\tilde{n}_{sustrate}$ represents the complex refractive index of the dielectric medium, $\tilde{n}_{dialectic}$ represents the complex refractive index of dielectric medium n$_{air}$ represents the refractive index of air and has a volumetric fractions of the substrate and dielectric media, respectively, in the layer 430.

The component mediums in the layer 432 are the substrate material, polysilicon, and the dielectric material. The effective refractive index of the homogeneous layer 444, corresponding to the composite layer 432, can be expressed as follows:

$$\tilde{n}_4 = f_4(\tilde{n}_{substrate}, \tilde{n}_{polysilicon}, \tilde{n}_{dielectric}, V_{substrate4}, V_{dielectric4}) \quad (11)$$

where $\tilde{n}_4$ represents the complex refractive index of the homogeneous layer 444, $\tilde{n}_{substrate}$ represents the, complex refractive index of the substrate medium, $\tilde{n}_{polysilicon}$ represents the complex refractive index of the polysilicon medium, $\tilde{n}_{dielectric}$ represents the complex refractive index of the dielectric medium, and V$_{substrate4}$ and V$_{dielectric4}$ represent the volumetric fractions of the substrate, and dielectric media, respectively, in the layer 432.

The component mediums in the layer, 434 are the substrate material and polysilicon. The effective refractive index of the homogeneous layer 446, corresponding to the composite layer 434, can be expressed as follows:

$$\tilde{n}_5 = f_5(\tilde{n}_{substrate}, \tilde{n}_{polysilicon}, V_{substrate}) \quad (12)$$

where $\tilde{n}_5$ represents the complex refractive index of the homogeneous layer 446, $\tilde{n}_{substrate}$ represents the complex refractive index of the substrate medium, $\tilde{n}_{polysilicon}$ represents the complex refractive index of the polysilicon medium, and V$_{substrate5}$ represents the volumetric proportion of the substrate medium in the layer 434.

The functions $f_1$, $f_2$, $f_3$, $f_4$, and $f_5$ in equations (8) through (12) can be determined using an appropriate one of several different homogenization formalisms. Examples of homogenization formalisms include, but are not limited to, Biot-Aragot rule, Maxwell-Garnett formalism, and Bruggeman formalism. The BiotAragot rule may be too simplistic a rule to be useful for most of the applications of interest here, while the Maxwell-Garnett is generally applicable to dilute mixtures of inclusions in a host medium. In the preferred embodiment of this invention, the Bruggeman formalism is the method of choice since it is not subject to the limitations that the others are. A specific example of a Bruggemann formalism suitable for use in the present invention may be found in: "Low-permittivity Nanocomposite Materials Using Scultpured. Thin Film Technology," V. C. Venugopal, A. Lakhtakia, R. Messier, and J. -P. Kucera, J. Vac. Sci. Technol. B 18, 2000, pp.32–36. More general and detailed discussions of homogenization formalisms can be found in, for example, "Electromagnetic Fields in Unconventional Materials and Structures," John Wiley & Sons, Inc., pp. 39–81; "Selected Papers on Linear Optical Composite Materials," A. Lakhtakia (ed.), SPIE Optical Engineering Press (1996); "Handbook of Electromagnetic Materials: Monolithic and Composite Versions and their Applications," P. S. Neelakanta; CRC Press (1995); "Selected Papers on Subwavelength Diffractive Structures," J. N. Mait and D. W. Prather, SPIE Optical Engineering Press (2001).

Once the laterally distinct regions are modeled as thin film stacks, their reflected fields can be calculated by setting up and solving a boundary value problem using Maxwell's equations or by using Fresnel equations. For a patterned substrate divided into p laterally distinct regions, the net reflectance from the patterned substrate can be calculated as a weighted incoherent sum of reflectances from the p laterally distinct regions constituting the pattern:

$$R = w_1(\lambda_0)|E_1|^2 + w_2(\lambda_0)|E_2|^2 + \ldots + w_p(\lambda_0)|E_p|^2 \quad (13)$$

where R is the net reflectance measured, E$_i$ are the individual incoherently adding field terms, w$_i$($\lambda_0$) are the weighting factors for the incoherently adding terms, and $\lambda_0$ is free-space wavelength of the incident light. The use of $|E_i|^2$ denotes the magnitude of the complex field E$_i$ in the frequency domain notation of electromagnetic field theory. Each individual incoherently adding term in equation (13) is the reflecting field of a thin film stack obtained by homogenizing composite layers in the laterally distinct regions. As in the case of the partial coherence reflectance model, a loss factor may also, be applied to the terms in equation (13) to account for losses due to non-specular reflection.

Figure 4E:
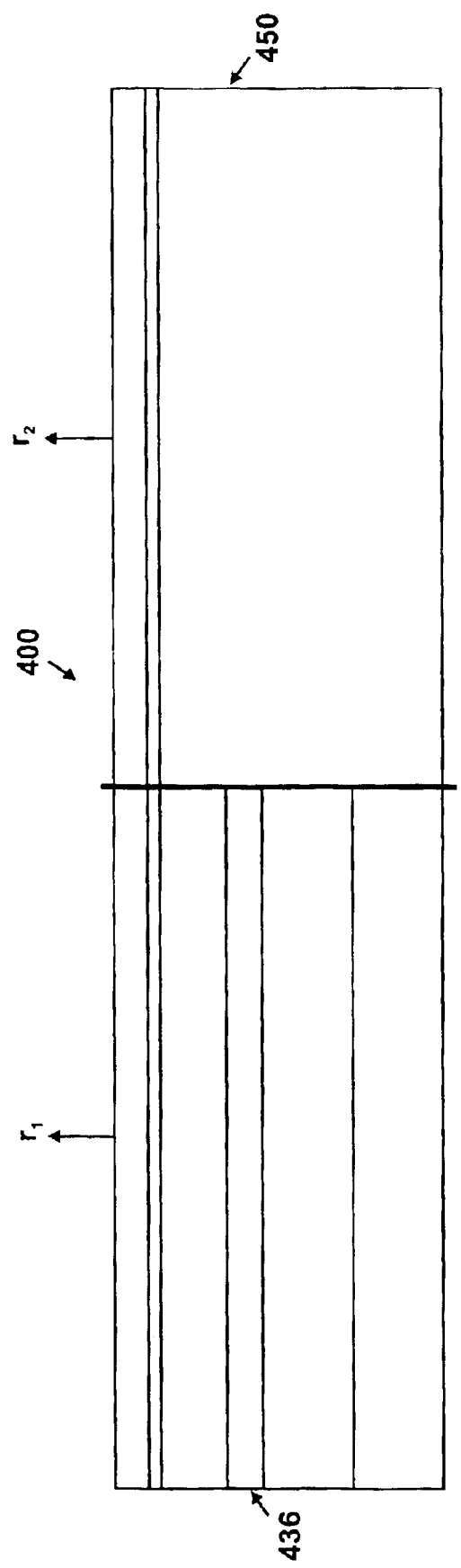
FIG. 4E shows the two laterally distinct regions of the patterned substrate shown in FIG. 4A replaced with homogenized thin film stacks.

To illustrate how net reflectance is calculated using the effective medium approximation model, consider FIG. 4E which shows the laterally distinct regions (402, 404 in FIG. 4A) of the patterned substrate 400 replaced with homogenized thin film stacks 436, 450, respectively. Let r$_1$ represent the reflected field due to the thin film stack 436, and let r$_2$ represent the reflected field due to the thin film stack 450. From equation (13), the net reflectance from the patterned substrate 400 is:

$$R_{400} = w_{436}(\lambda_0)|E_{436}| + w_{450}(\lambda_0)|E_{450}|^2 \quad (14)$$

where R$_{400}$ is the net reflectance from the patterned substrate 400, E$_{436}$, E$_{450}$ are the individual incoherently adding field terms from the thin film stacks 436, 450, respectively, and w$_{436}$($\lambda_0$), w$_{450}$($\lambda_0$) are the weighting factors for the incoherently adding terms. If w$_{436}$ is replaced with 1−w$_{450}$, then equation (14) becomes:

$$R_{400} = (1-w_{450}(\lambda_0))|E_{436}|^2 + w_{450}(\lambda_0)|E_{450}|^2 \quad (15)$$

Figure 5:
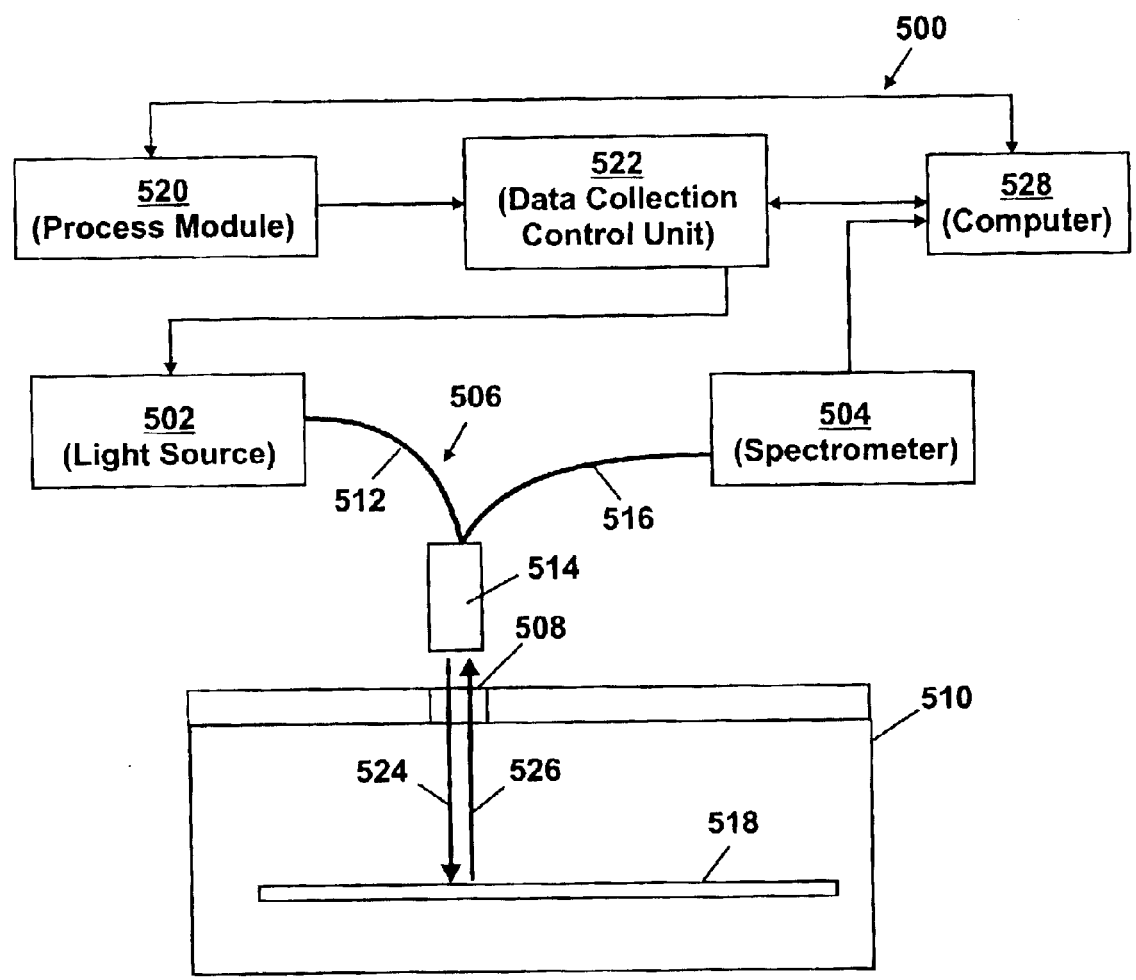
FIG. 5 shows a process setup according to an embodiment of the invention.

FIG. 5 is a simplified schematic of a system 500 for detecting an endpoint in processing of a patterned substrate. The system includes a light source 502 for generating a light beam, a spectrometer 504 for detecting and analyzing a light beam, and an optical system 506 for transporting light to and form a port 508 at the top of a process chamber 510. For example, the optical system 506 could include an optical fiber 512 that transports light from the light source 502 to a collimator 514, where the collimator 514 is mounted above the port 508, and an optical fiber 516 that transports light from the collimator 514 to the spectrometer 504. A semiconductor substrate 518 is mounted inside the process chamber 510. To avoid obscuring the invention, the details of the equipment for processing the substrate 518 are not shown. However, it would be obvious to one of ordinary skill in the art what equipment is needed to process the substrate. For example, if a recess is to be formed in the substrate via plasma etching, the substrate 518 would be mounted on a chuck (not shown) in the process chamber 510, and the appropriate equipment for generating the plasma would be provided.

In operation, a process module 520 that controls processing of the semiconductor substrate 518 sends a signal to a data collection control unit 522 to trigger operation of the light source 502. When the light source 502 is triggered, it generates a light beam, which is transported through the optical fiber 512 to the collimator 514. The operating wavelength band of the light source 502 is selected to be in the region where sensitivity to the parameters of interest is heightened. In general, a broader range is more useful. In one example, the wavelength range of the light source 502 is 190 to 800 nm. Wavelengths up to 1000 nm and greater can also be used. The light beam 524 leaves the collimator 514, passes through the port 508, and strikes the substrate 518 at normal incidence. The collimator 514 collects the light beam 526 reflected normally from the substrate 518. The reflected light beam 526 travels to the spectrometer 504 through the optical fiber 516. The spectrometer 504 analyzes the; reflected light beam 526 and sends data representative of the net reflectance spectrum of the substrate 518 to a computer 528 for further analysis.

In one embodiment, the computer 528 includes the partial coherence reflectance model and the effective medium approximation model for calculating the net reflectance spectrum of a patterned substrate, such as semiconductor substrate 518, and a routine that searches for an optimal set of parameters that provides a match, between the modeled net reflectance spectrum and the measured net reflectance spectrum received from the spectrometer 504. In one embodiment, the search routine is a non-linear regression routine, such as Levenberg-Marquardt Compromise. However, other types of search routines, such as multivariate regression analysis or neural net matching, can also be used. The set of parameters obtained can be mapped to several key quantities of interest, such as mask layer thickness starting etch depth, recess depth, and trench depth. The quantities of interest can be used to determine an endpoint in processing of the patterned substrate, as will be further described below.

Figure 6A:
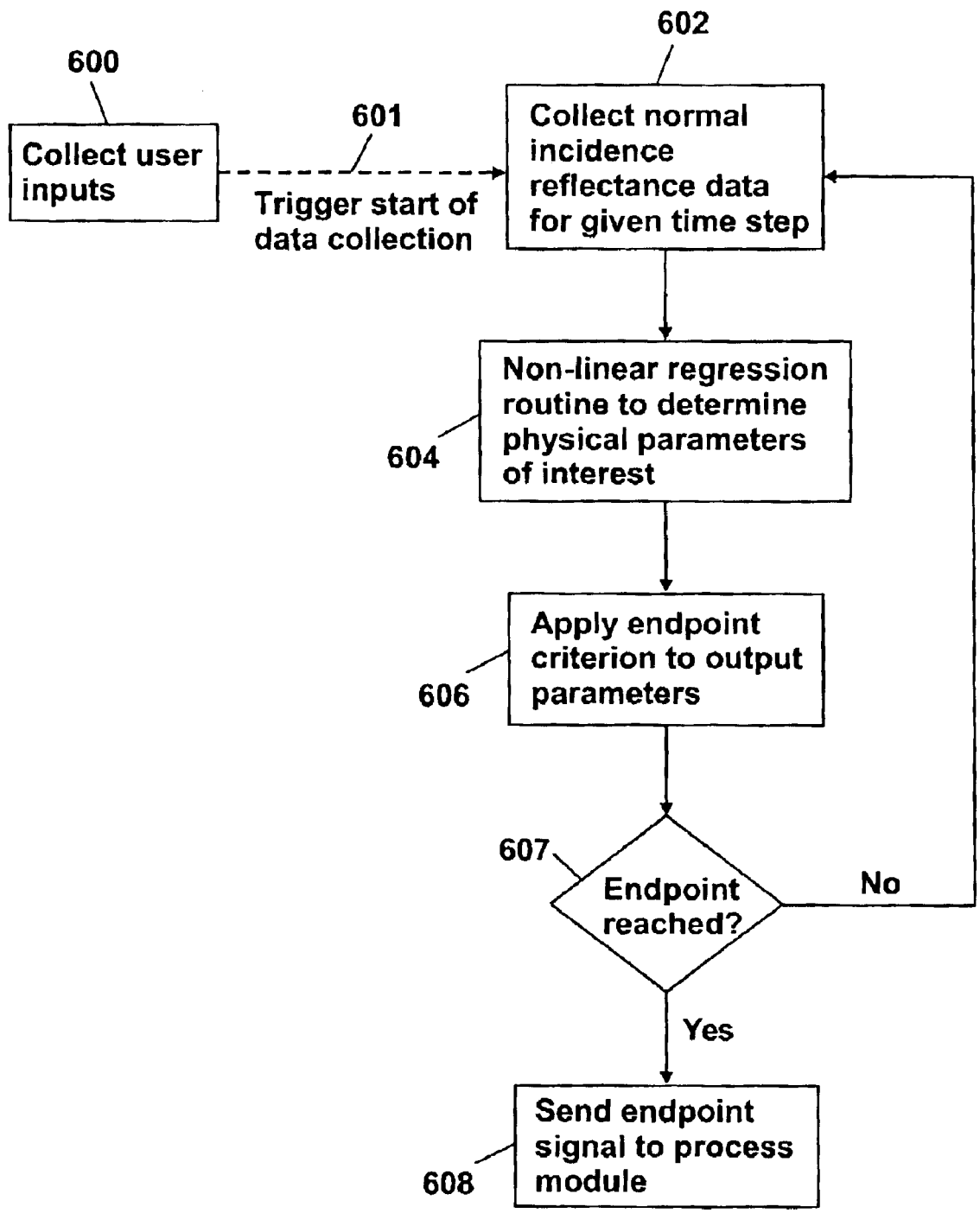
FIG. 6A is an overview of a process for detecting an endpoint in a patterned substrate processing step according to an embodiment of the invention.

FIG. 6A is an overview of a process for collecting normal reflectance data from a substrate according to an embodiment of the invention. One objective is to improve a high-quality reflectance signal even in the presence of significant background light levels such as the emission from a luminous plasma. At the start of the process, a set of user inputs are collected (600). The user inputs contain the information necessary to, set up the endpoint detection algorithm. After collecting the user inputs, data collection is triggered (601). Normal incidence reflectance data is collected from the substrate over a given time interval (602). After collecting the reflectance data, a non-linear regression routine is used to compute an optimal set of parameters that provides the closest match between the reflectance data and the modeled reflectance spectrum of the substrate (604). Then, an endpoint criterion is applied: to the parameters (606). For an etching process, for example, an endpoint criterion could be whether the etch depth is greater than or equal to the target etch depth. The system checks whether the endpoint criterion is satisfied (607). If the endpoint criterion is satisfied, a signal indicating a process endpoint is sent to the process module (608). Otherwise, the system returns to step 602.

Figure 6B:
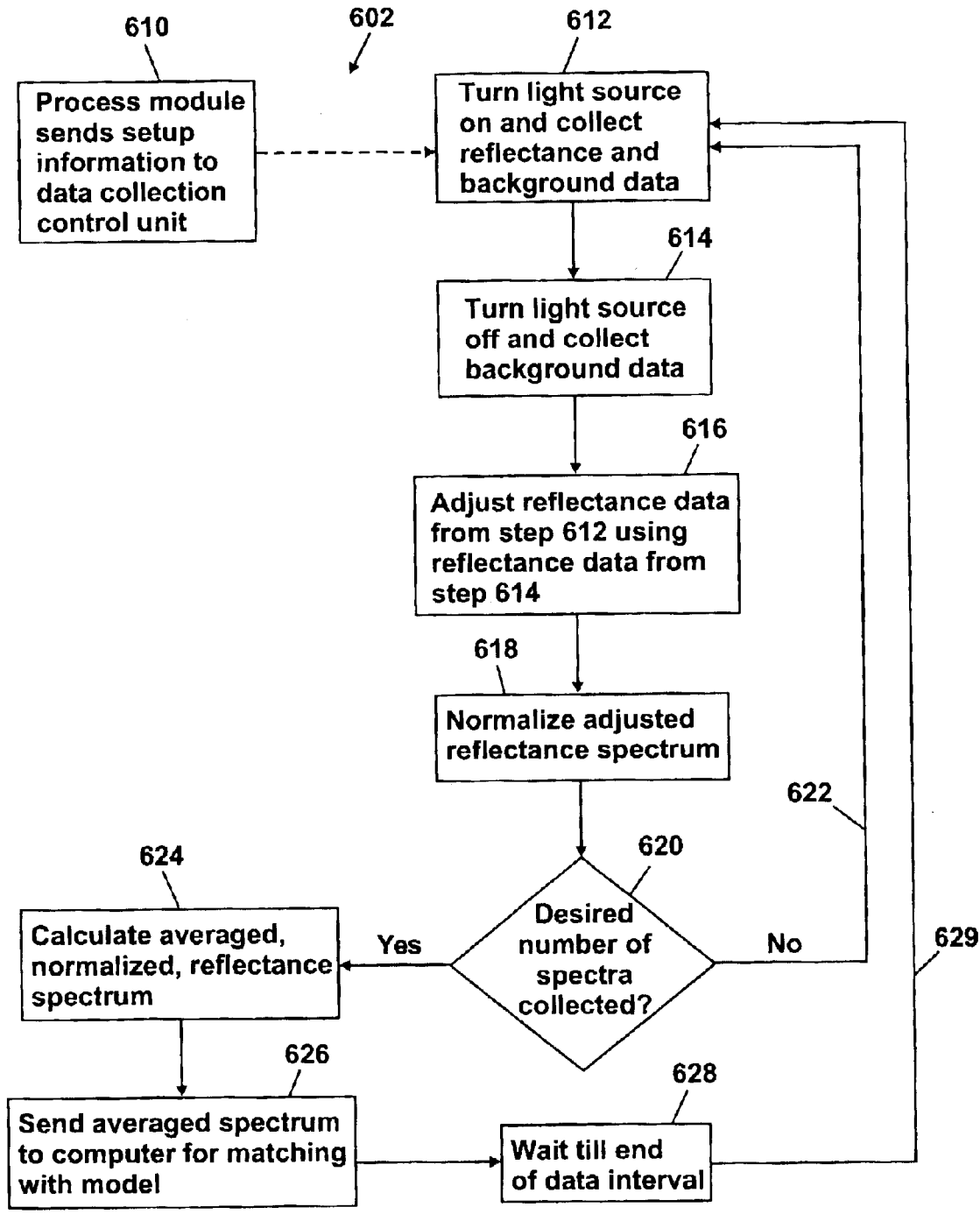
FIG. 6B is an overview of a process for collecting normal incidence reflectance data according to an embodiment of the invention.

FIG. 6B is a flowchart elaborating on step 602 of FIG. 6A, i.e., normal incidence reflectance data collection in situ. Prior to the start of data collection, the process module (520 in FIG. 5) informs the data collection control unit (522 in FIG. 5) about how the data should be collected and calibrated (610). For example, the process module tells the data collection control unit how often to collect the reflectance data from the substrate and the number of reflectance spectra to collect for each time step. The process module also gives the data collection control unit a baseline reflectance spectrum, typically; a bare silicon reflectance spectrum, for calibration of the measured reflectance spectra. The bare silicon reflectance spectrum is collected prior to processing the substrate.

When the data collection control unit (522 in FIG. 5) receives instruction to start collecting data, the light source (502 in FIG. 5) is turned on to generate a light beam, which is directed to strike the substrate, and the spectrometer (504 in FIG. 5) collects reflectance data from the substrate (612). Then, the light source is turned off and the spectrometer again collects reflectance data from the substrate (614). When the light source is turned off, the data collected by the spectrometer is due to background sources, such as from plasma emissions, and detector noise. The next step is to subtract the reflectance data obtained in step 614 from the reflectance data obtained in step 612 to remove the contribution of the background sources.

The corrected reflectance spectrum is normalized by the baseline spectrum (618). Then, the system checks if the desired number of spectra has been collected for the current time step (620). If the desired number of spectra has not been collected, the system returns to step 612 and starts collecting data for another reflectance spectrum (622). If the desired number of spectra has been collected, the system computes an average of the collected spectra to obtain an averaged, normalized, reflectance spectrum (624). The averaged reflectance spectrum is sent to the computer (528 in FIG. 5) for matching with the modeled reflectance spectrum of the substrate (626). After sending the averaged reflectance spectrum to the computer, the system waits for the end of the current time step (628). At the end of the current time step, the system returns to step 612 to start collecting data for the next time step (629).

Figure 6C:
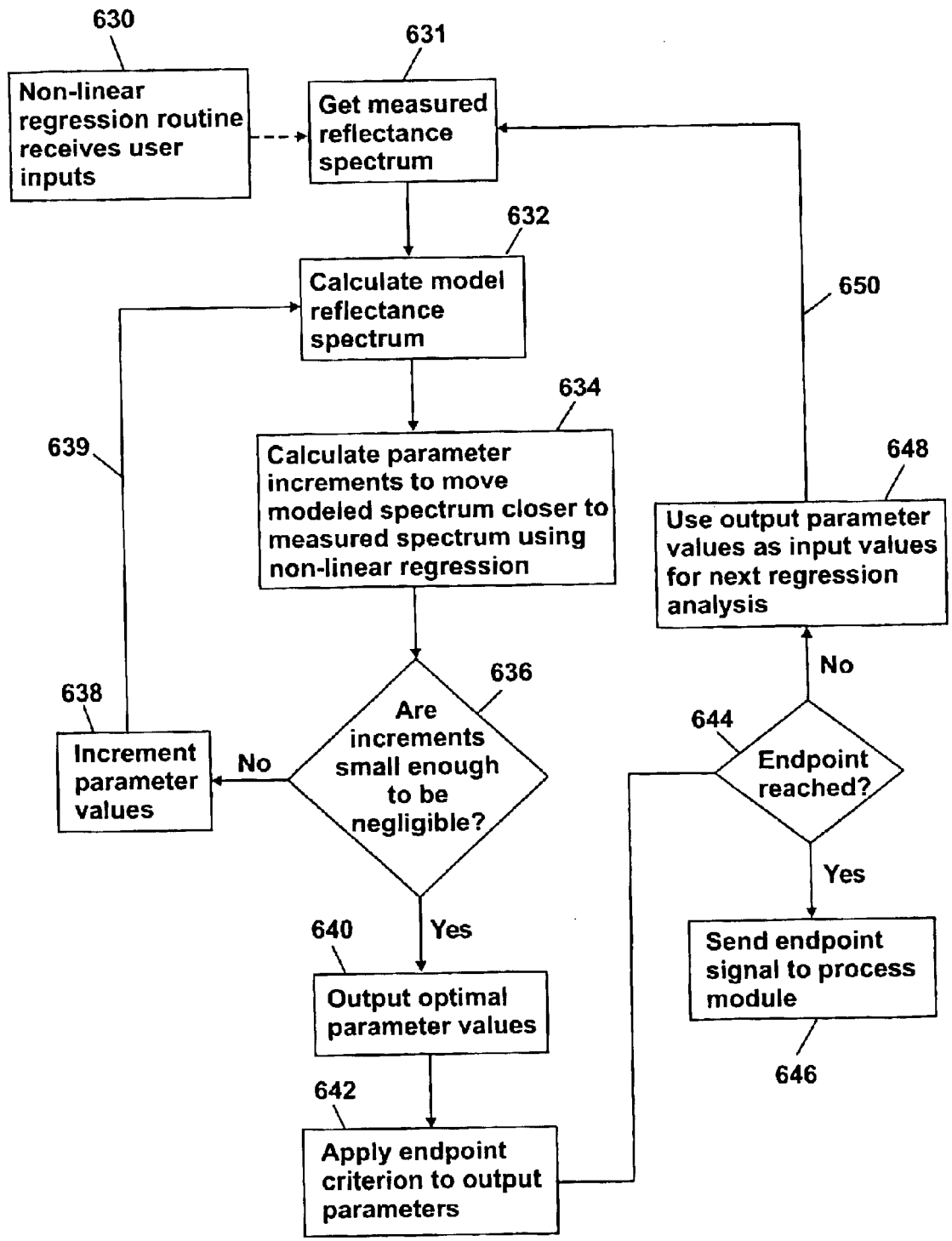
FIG. 6C is an overview of a process for matching measured reflectance spectrum to modeled reflectance spectrum according to an embodiment of the invention.

FIG. 6C is a flowchart elaborating on step 604 of FIG. 6A, i.e., non-linear regression analysis one objective is to quickly reach a converged set of parameter values by incrementally stepping the parameter values in the appropriate direction through the parameter space till the solution is reached. Prior to start of the non-linear regression analysis, user inputs are received by the non-linear regression routine (630). The user inputs include initial guesses for the parameters to be determined by matching the measured reflectance spectrum to the modeled reflectance spectrum. The non-linear regression routine also receives the (averaged) measured reflectance spectrum (631). Next, the modeled reflectance spectrum is calculated (632). Then, the non-linear regression routine is used to calculate increments to the set of parameters to move closer to the best match between the measured reflectance spectrum and the modeled reflectance spectrum (634).

The system checks whether the increments calculated in step 634 are small enough to be negligible (636). If the increments are not small enough to be negligible, the system increments the values of the parameters and returns to step 632 to recalculate the modeled spectrum using the new parameter values (638). If the, increments are small enough to be negligible, the system outputs the optimal parameter values (640). The physical parameters of interest, e.g., recess depth, are extracted from the optimal parameter values (642). Then, an endpoint criterion is applied to the physical parameters. For example, an endpoint criterion could be that the recess depth is within a certain tolerance from the target depth. The algorithm checks if the endpoint criterion is satisfied (644). If the endpoint criterion is satisfied, a signal is sent to the process module (646). If the endpoint criterion is not satisfied, the next measured reflectance spectrum is obtained and the non-linear regression analysis is repeated (648). The parameter values, obtained for the current time step are used as initial guesses for the next non-linear regression analysis (650) to speed up the non-linear regression routine.

Although not explicitly stated at step 632, it should be clear that the user inputs also include information about how to divide the substrate into laterally distinct areas. The user inputs also include optical properties of each layer (or material) in the laterally distinct area so that reflected fields from thin film stacks corresponding to the laterally distinct area can be calculated, as previously described. Before the start of each regression analysis, the reflected fields are recomputed because the structure of the thin film stacks may have changed during processing of the substrate, consequently resulting in changes in the values of the weighting factors and coupling factors in the net reflectance equations discussed above. The user inputs may also include an initial guess of the transition wavelength, which determines the portion of the reflectance spectrum where the partial coherence reflectance model and the effective approximation model would be applied.

Figure 7A:
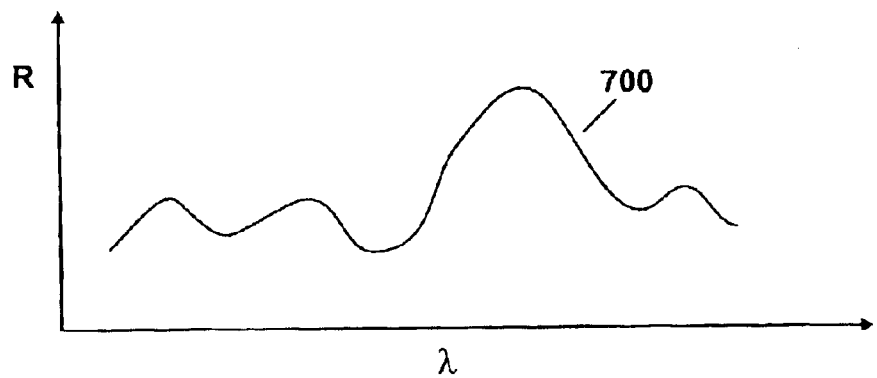
FIG. 7A is a schematic of a measured reflectance spectrum.
Figure 7B:
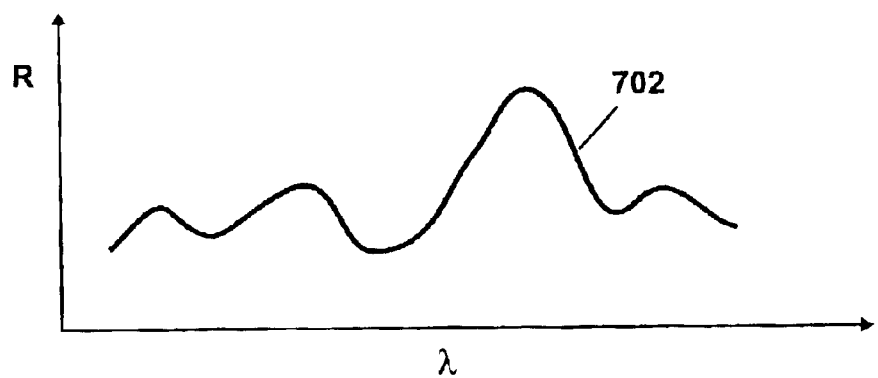
FIG. 7B is a schematic of a modeled reflectance spectrum.
Figure 7C:
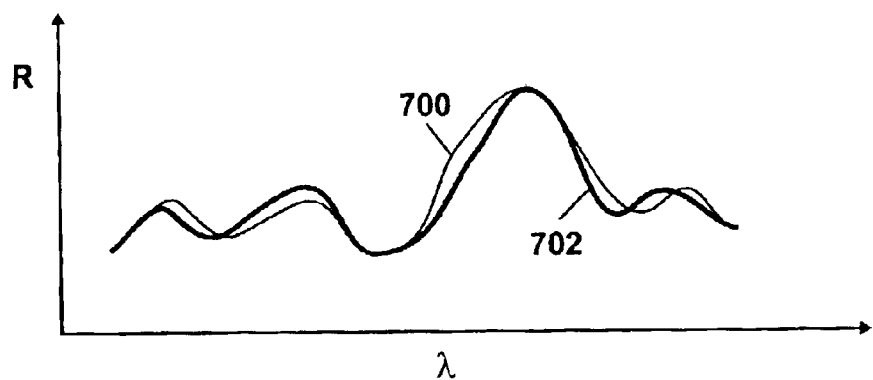
FIG. 7C is an illustration of a match between the measured reflectance spectrum of FIG. 7A and the modeled reflectance spectrum of FIG. 7B.

In one embodiment, the invention uses a modified version of a non-linear regression technique called the Levenberg-Marquardt Compromise to quickly and accurately-locate optimal values of key parameters starting from the initial guesses of the parameter values. Although, the Levenberg-Marquardt Compromise technique is the preferred technique, other techniques, such as multivariate regression analysis and neural net approaches, may also be employed, to extract key parameters of interest. To illustrate how the non-linear regression routine works, FIG. 7A shows a measured reflectance spectrum 700 and FIG. 7B shows a modeled reflectance spectrum 702 computed using initial guesses from user inputs. The first step in the non-linear regression routine is to calculate a least squares difference error metric between the two reflectance spectra 700, 702. FIG. 7C shows the measured reflectance spectrum 700 superimposed on the modeled reflectance spectrum 702. The least squares difference is computed by taking several points across the wavelength range, calculating the vertical difference between the spectra 700, 702 at each point, and summing the square of the differences at all the points. The least squares difference error metric is then used to determine the increments for the parameter values.

So far, the description of the non-linear regression analysis above is standard. Now, what happens in many cases is that a lot of the parameters that are not of interest cause significant changes in the entire modeled spectrum While the parameters of interest cause changes in small regions of the modeled spectrum. To allow the parameter values; of interest, to be located quickly and accurately, the differences in the regions of the spectrum where the parameters of interest are expected to make a difference are amplified by a, factor, e.g., $(1+\gamma_i)$, prior to summing the square of the differences at all the points. Thus, the least squares difference error is larger if the differences in the region of interest are larger. A constant or weighting factor may also be applied to the amplification factor to further bias the least squares difference error.

Figure 8:
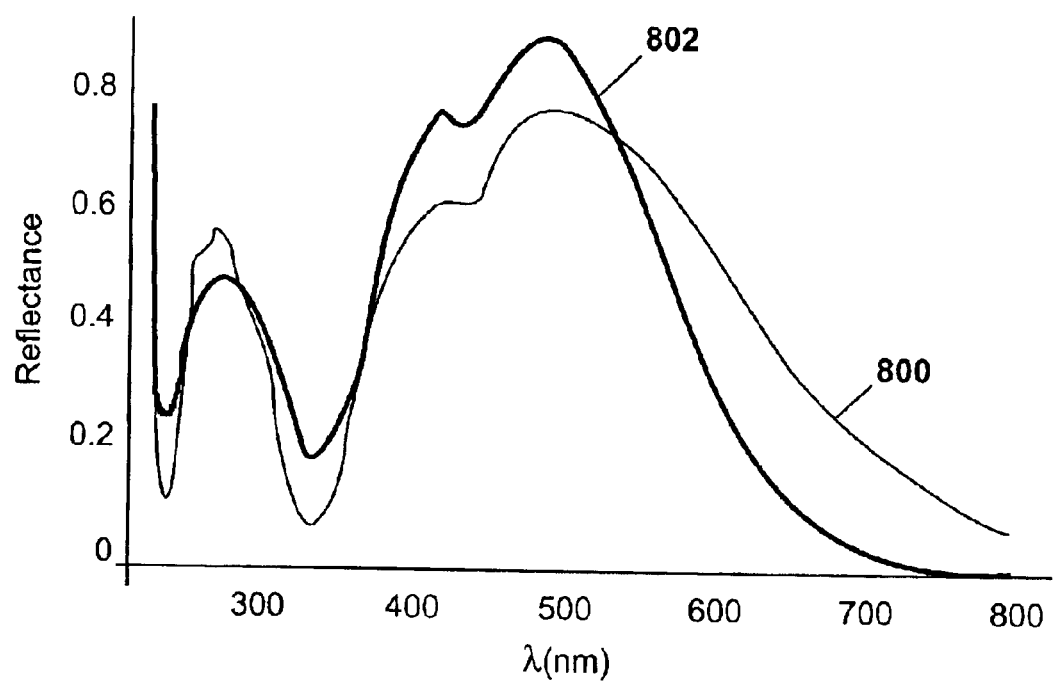
FIG. 8 is an illustration of a match between a measured net reflectance spectrum and a modeled net reflectance spectrum obtained by a combination of partial coherence reflectance and effective medium approximation models.

FIG. 8 illustrates a match between a modeled reflectance spectrum 800 computed using a combination of the partial coherence reflectance model and the effective medium approximation model and a measured reflectance spectrum 802. The patterned substrate in this example includes deep recess structures, approximately 243 nm deep. The range of wavelengths used was 225 to 800 nm. The transition wavelength was determined to be approximately 410 nm. What this means is that the portion of the modeled spectrum 802 above 410 nm is calculated using the effective medium approximation model, and the portion of the modeled reflectance spectrum below the transition wavelength is calculated using the partial coherence reflectance model. As previously mentioned, the user can provide an initial guess for the transition wavelength. This initial guess could be a value in the neighborhood of the lateral extent of the dominant features on the patterned substrate. This value can be adjusted based on the vertical dimension of the features. This value can be further adjusted in real time based on the match quality between the measured spectrum and the modeled spectrum.

As can be appreciated from the above, the invention provides several advantages. For example, a patterned substrate having a random array of features can be monitored in situ using a method of the invention. The invention provides a combination of optical models that can be used to calculate a modeled reflectance spectrum of the patterned substrate. Parameters of interest related to the processing of the substrate can be determined by matching the modeled reflectance spectrum to a measured reflectance spectrum. The optical models are valid in different regimes of the reflectance spectrum, allowing an optimal match between the modeled reflectance spectrum and the measured reflectance spectrum. The optical models are robust in that they do not place any restrictions on arrangement of features on the patterned substrate, i.e., the models are not limited to patterned substrates having special test features and can be applied to patterned substrates having a complex array of random features. The models can accommodate incoming material variations, such as layer thicknesses, starting trench depth variation, and differences in pattern density and substrate orientation. The invention uses a biased non-linear regression technique to focus on key parameters of interest much more accurately, thus improving the sensitivity of the system.

While the invention has been described in terms of several preferred embodiments, there are alterations, permutations, and equivalents which fall within the scope of this invention. For example, other techniques can be used to match the measured reflectance spectrum to the modeled reflectance spectrum besides the Levenberg-Marquardt Compromise. Also, the transition wavelength could be at either extreme of the broadband spectrum at any given time in the patterned substrate processing so that only one of the optical models is active in computing modeled net reflectance spectrum. It is therefore intended that the following appended claims be interpreted as including all such alterations, permutations, and equivalents as fall within the true spirit and scope of the invention.

What is claimed is:

1. A method of determining a parameter of interest during processing of a patterned substrate, comprising:

obtaining a measured net reflectance spectrum resulting from illuminating at least a portion of the patterned substrate with a light beam having a broadband spectrum;

calculating a modeled net reflectance spectrum as a weighted incoherent sum of reflectances from different regions constituting the portion of the patterned substrate, for wavelengths below a selected transition wavelength in the broadband spectrum, using a first optical model to calculate the reflectance from each region as a weighted coherent sum of reflected fields from thin film stacks corresponding to laterally distinct areas constituting the region;

for wavelengths above the selected transition wavelength in the broadband spectrum, using a second optical model to calculate the reflectance from each region as a reflected field from a thin film stack obtained by replacing layers in the region with effective homogeneous mediums; and determining a set of parameters that provides a close match between the measured net reflectance spectrum and the modeled net reflectance spectrum.

2. The method of claim 1, wherein the transition wavelength is functionally dependent on dimensions of dominant features on the patterned substrate.

3. The method of claim 1, wherein determining the set of parameters comprises determining in-situ an optimal value for the transition wavelength.

4. The method of claim 1, wherein a free-space wavelength of the light beam is comparable to or smaller than a characteristic size of dominant features in the portion of the patterned, substrate at wavelengths below the transition wavelength.

5. The method of claim 4, wherein the free-space wavelength is at least 2.0 times the characteristic size.

6. The method of claim 1, wherein a free-space wavelength of the light beam is larger than a characteristic size of dominant features in the portion of the patterned substrate at wavelengths above the transition wavelength.

7. The method of claim 6, wherein the free-space wavelength is greater than 2.0 times the characteristic size.

8. The method of claim 1, further comprising extracting the parameter of interest from the set of parameters.

9. The method of claim 8, wherein the parameter of interest is a vertical dimension of a feature in the portion of the patterned substrate.

10. The method of claim 1, wherein the thin film stacks corresponding to the laterally distinct areas in the first optical model are isotropic and homogeneous.

11. The method of claim 1, wherein using the first optical model to calculate the reflectance comprises modeling the portion of the patterned substrate as having a nominally polarization-independent reflectance.

12. The method of claim 1, further comprising applying a loss factor to the modeled net reflectance that is proportional to non-specular reflection from the portion of the patterned substrate prior to determining the set of parameters.

13. The method of claim 1, wherein replacing layers in the region with effective homogeneous mediums comprises modeling features in the portion of the patterned substrate as inclusions in the homogeneous mediums.

14. The method, of claim 1, wherein determining the set of parameters comprises calculating a least squares difference error metric between the measured net reflectance spectrum and the modeled net reflectance spectrum and finding the set of parameters that minimizes the error metric.

15. The method of claim 14, further comprising amplifying an effect of a change in the parameter of interest on the error metric.

16. The method of claim 14, wherein calculating the modeled net reflectance spectrum comprises receiving a set of initial guesses for the set of parameters.

17. The method of claim 1, wherein obtaining the measured net reflectance spectrum comprises obtaining a set of reflectance spectra of the portion of the patterned substrate over a time interval and setting the measured net reflectance spectrum to an average of the set of reflectance spectra.

18. A method of controlling processing of a patterned substrate, comprising:

obtaining a measured net reflectance spectrum resulting from illuminating at least a portion of the patterned substrate with a light beam having a broadband spectrum;

calculating a modeled net reflectance spectrum as a weighted incoherent sum of reflectances from different regions constituting the portion of the patterned substrate:

for wavelengths below a selected transition wavelength in the broadband spectrum, using a first optical model to calculate the reflectance from each region as a weighted coherent sum of reflected fields from thin film stacks corresponding to laterally distinct areas constituting the region;

for wavelengths above the selected transition wavelength in the broadband spectrum, using a second optical model to calculate the reflectance from each region as a reflected field from a thin film stack obtained by replacing layers in the region with effective homogeneous mediums;

determining a set of parameters that provides a close match between the measured net reflectance spectrum and the modeled net reflectance spectrum;

deriving a parameter of interest from the set of parameters; and signaling an endpoint in the processing of the patterned substrate if the value of the parameter of interest satisfies a predetermined endpoint criterion.

19. A method of determining a high-aspect ratio parameter of interest during processing of a patterned substrate, comprising:

obtaining a measured net reflectance spectrum resulting from illuminating at least a portion of the patterned substrate with a light beam having a broadband spectrum;

calculating a modeled net reflectance spectrum as a weighted incoherent sum of reflectances from different regions constituting the portion of the patterned substrate;

for wavelengths below a selected transition wavelength in the broadband spectrum, using a first optical model to calculate the reflectance from each region as a weighted coherent sum of reflected fields from thin film stacks corresponding to laterally distinct areas constituting the region;

for wavelengths above the selected transition wavelength in the broadband spectrum, using a second optical model to calculate the reflectance from each region as a reflected field from a thin film stack obtained by replacing layers in the region with effective homogeneous mediums; and determining a set of parameters that provides a close match between the measured net reflectance spectrum and the modeled net reflectance spectrum.

* * * * *